(12) United States Patent
Manela

(10) Patent No.: US 10,628,942 B2
(45) Date of Patent: Apr. 21, 2020

(54) SYSTEM AND METHOD FOR USE IN DIAGNOSTICS OF EYE CONDITION

(71) Applicant: Israel Manela, Nahariya (IL)

(72) Inventor: Israel Manela, Nahariya (IL)

( * ) Notice: Subject to any disclaimer, the term of this patent is extended or adjusted under 35 U.S.C. 154(b) by 117 days.

(21) Appl. No.: 16/063,277

(22) PCT Filed: May 9, 2017

(86) PCT No.: PCT/IL2017/050507
§ 371 (c)(1),
(2) Date: Jun. 17, 2018

(87) PCT Pub. No.: WO2017/203510
PCT Pub. Date: Nov. 30, 2017

(65) Prior Publication Data
US 2019/0180437 A1    Jun. 13, 2019

(30) Foreign Application Priority Data

May 26, 2016 (IL) .......................... 245879

(51) Int. Cl.
*G06T 7/00* (2017.01)
*A61B 3/113* (2006.01)
(Continued)

(52) U.S. Cl.
CPC .......... *G06T 7/0012* (2013.01); *A61B 3/0058* (2013.01); *A61B 3/0091* (2013.01); *A61B 3/09* (2013.01); *A61B 3/103* (2013.01); *A61B 3/113* (2013.01); *A61B 3/12* (2013.01); *A61B 3/14* (2013.01); *A61B 3/18* (2013.01);
(Continued)

(58) Field of Classification Search
CPC .......... G06T 7/0012; G06T 7/62; G06T 7/90; G06T 2207/10024; G06T 2207/30041; G06T 2207/30242; A61B 3/08; A61B 3/085; A61B 3/0058; A61B 3/0091;
(Continued)

(56) References Cited

U.S. PATENT DOCUMENTS 5,555,039 A    9/1996 Iki et al.
8,783,871 B2   7/2014 Pamplona et al.
(Continued)

*Primary Examiner* — Collin X Beatty

(57) ABSTRACT

A system for use in diagnostics of eye condition is described, the system comprises a pair of eye inspection units configured for inspection of each of user's eyes and a control unit. The eye inspection units comprise: a display unit comprising a display panel configured to display one or more selected images to a user's and an optical path unit located in optical path between the display panel and a user's eye and configured for selectively controlling light ray propagation towards the user's eye; an eye tracking module configured to generate data about of location and orientation of a user's eye thereby providing data indicative of gaze direction of the user's eye; an optical power detection unit configured and operable for obtaining and determining data indicative of optical power of the user's eye. The control unit is configured and operable to operate the eye inspection units to determine data inductive of at least one of eye accommodation to object in close proximity, convergence of line of sight of the user's eyes and a level of fusion of image data received by both eyes of the user.

11 Claims, 7 Drawing Sheets

(51) Int. Cl.

| | |
|---|---|
| *A61B 3/12* | (2006.01) |
| *A61B 3/09* | (2006.01) |
| *A61B 3/103* | (2006.01) |
| *G06T 7/62* | (2017.01) |
| *G06T 7/90* | (2017.01) |
| *A61B 3/00* | (2006.01) |
| *A61B 3/14* | (2006.01) |
| *A61B 3/18* | (2006.01) |

(52) U.S. Cl.
CPC ................. *G06T 7/62* (2017.01); *G06T 7/90* (2017.01); *G06T 2207/10024* (2013.01); *G06T 2207/30041* (2013.01); *G06T 2207/30242* (2013.01)

(58) Field of Classification Search
CPC ........... A61B 3/09; A61B 3/103; A61B 3/113; A61B 3/12; A61B 3/14; A61B 3/18
USPC ........................................................ 351/206
See application file for complete search history.

(56) References Cited

U.S. PATENT DOCUMENTS

| | | | |
|---|---|---|---|
| 8,807,749 B2 * | 8/2014 | Fateh | A61B 3/00 351/205 |
| 2014/0211167 A1 | 7/2014 | Lewis | |
| 2014/0218685 A1 | 8/2014 | Nakamura | |
| 2015/0125052 A1 * | 5/2015 | Wong | G06K 9/46 382/128 |

* cited by examiner

SYSTEM AND METHOD FOR USE IN DIAGNOSTICS OF EYE CONDITION

TECHNOLOGICAL FIELD

The invention is in the field of eye inspection and is particularly relevant for use in diagnostics of eye condition in a patient by physicians and/or optometrists.

BACKGROUND

Vision impairments and vision related health issues affecting the worldwide population in growing rates. Other than myopia and other visual impair, the human eyes are affected by long hours of work in front of a computer screen, as well as providing a window to internal pathologies. For example:

Computer Vision Syndrome (CVS) describes strain related eye condition resulting from patient's focusing on a digital display for long hours. This is a result of eyes' focusing on objects at relatively close distance as well as the digital appearance of the displayed data. CVS may be associated with symptoms like eye strain, headaches, blurred vision, dry eyes as well as pain in the neck and shoulders.

Macular degeneration, and in particular Age-related Macular Degeneration (AMD), is one of the largest causes for acquired blindness. AMD is typically caused by accumulation of waste protein in the retina at the macular region and generation of waste deposits under the retina, generally called Drusens.

The present diagnostic technique relate to data collection about symptoms (for CVS) as well as inspection of the retina by a physician. More accurate diagnosis generally requires the use of highly expensive tools and at times inspection of the eye under anesthesia.

GENERAL DESCRIPTION

Diagnosis of various conditions such as computer vision syndrome (CVS), accumulation of waste protein within the retina associated with age-related macular degeneration (AMD), and other medical condition is highly important for providing effective treatment. Further, early diagnosis can provide early treatment as well as a research tool linking known conditions with other health conditions, such as Alzheimer or Cardiovascular diseases that might have common pathology. As indicated above, the currently available diagnosis techniques are generally qualitative and are subjected to physician interpretation. Advanced techniques capable of providing data about condition of the retina, which are used in follow-up of AMD patients like optical coherent tomography (OCT), are highly expensive and are only available in large medical facilities. Further operation of OCT systems require highly trained personal. This is while the system and technique of the present invention are preferably configured to provide substantially computerized test that can be performed by any person and provide a relatively simple and low-cost inspection system.

The present invention provides a system and method for use in diagnosis of eyes' condition and related visual conditions of a patient. The system is configured to simplify the diagnosis process and thus allow discovery of various conditions at early stages, as well as providing measureable data allowing comparative inspection that is unrelated to subjective interpretation of a physician. Additionally, the system of the invention is preferably configured to be of relatively small form factor and to provide measurable output data to thereby enable accurate diagnosis and follow-up of patients' condition.

The system is generally configured to provide measured data related to eyes' movement and focusing functions and in some configuration to provide data about internal eye condition. To this end, the system is configured and operable to provide image display data to each of the patient's eye separately, to thereby enable three-dimensional display of a predetermined scene or object, while determining data about patient's eye state and condition. The data about patient's eye and condition may generally include data about angular orientation of each of the patient's eyes and data about optical power provided by each of the corresponding eye lens and accommodation of the lens in the user's eyes to objects' distance.

More specifically, the system is configured for displaying to the patient one or more objects arriving from large distance (both in relative orientation with respect to each eye's display and in ray propagation and effective/virtual object plane) and for determining data about eyes' orientation and optical power. The system is further configured for processing data associated with eyes' orientation and optical power together with data about the displayed images to the patient to determine data about eye condition of the patient. The data associated with eye condition of the patient may generally comprise data about at least one of the following: accommodation of the eyes' optical power to objects at close distances, patients' eyes convergence towards objects at close distance, and image fusion performed by the patient to allow interpretation of a single image from data collected by both eyes.

According to another aspect of the invention, the system may include an imaging unit (camera unit) aligned with optical axis of each of the patient's eyes and configured for collecting image data indicative inner surface of the patient's eyes, typically around the macula of the patient. The collected image data may generally be indicative of a region of radius of at least 2 millimeters around the macula of each of the patient's eye, and preferably a region of radius of 3-4 millimeters around the macula. The system may process the collected image data to determine state of macular degeneration. Data about state of macular degeneration may comprise at least one, and preferably more than one, of the following data pieces: indication about existence of one or more drusens within a predetermined radius around the macula; number of drusens within predetermined radius, size of each detected drusen, color of each detected drusen etc. In this connection it should be noted that the term drusen or drusens as referred to herein related to accumulation of protein waste with the retina of the eye, typically indicating macular degeneration. It should further be noted that the technique of the present invention may be configured for processing and analyzing the collected image data for identifying any abnormality within the macular region that can be manifested in collected optical image data.

The system generally comprises a pair of eye inspection units, each comprising an eye tracking unit, an autorefractor unit (auto-refractometer unit), and a display unit and is associated with a control unit. The display unit comprises a display panel and an optical path unit located in optical path between the display panel and the user's eye. The optical path unit is configured for transmitting light output of the display panel towards the user's eye while varying light propagation to thereby vary location of (generally virtual) image plane and cause displayed images to appear as if coming from a selected distance generally different than that of the display panel. The optical path unit is typically configured to vary virtual image plane of the displayed image to appear at selected distances between 1 meter and higher and about 5 centimeters.

Additionally or alternatively, according to some embodiments, the system may include an eye tracking unit and a macular imaging (camera) unit configured to collect light arriving from the retina to generate image data associated with a region of the retina, generally a region around the macula. The macular imaging unit may include a light source, generally infra-red (IR) light source, configured to provide illumination to the retina and an imager unit configured to collect light (generally IR light) reflected from the retina to generate the associated image data.

In some configurations of the present invention, the eye inspection units may also include a raster unit configured to vary optical propagation path for at least the autorefractor/autorefractometer unit and for the illumination and collection paths of the macular imaging unit when used. More specifically, to provide accurate data about optical power, as well as accurate imaging of the macula within the user's eye, the autorefractor/autorefractometer and the macular imaging unit (when used) are preferably configured with optical axes thereof aligned with optical axis of the eye. Thus, the control unit may be configured to receive data about eye location and orientation from the eye tracking unit and vary orientation of the raster unit to align optical paths accordingly.

Thus, according to one broad aspect of the invention, there is provided a system for use in diagnostics of eye condition comprising a pair of eye inspection units configured for inspection of each of user's eyes and a control unit, said eye inspection units comprise:

- a display unit comprising a display panel configured to display one or more selected images to a user's and an optical path unit located in optical path between the display panel and a user's eye and configured for selectively controlling light ray propagation towards the user's eye;
- an eye tracking module configured to generate data about of location and orientation of a user's eye thereby providing data indicative of gaze direction of the user's eye;
- an optical power detection unit configured and operable for obtaining and determining data indicative of optical power of the user's eye;
- said control unit being configured and operable to operate said eye inspection units to thereby determine data inductive of at least one of eye accommodation to object in close proximity, convergence of line of sight of the user's eyes and a level of fusion of image data received by both eyes of the user. The eye inspection units may be configured in a head mounted package.

According to some embodiments said display unit and said optical power detection unit may be located along a general optical axis of the user's eye, said eye inspection unit comprises a beam splitting module configured for splitting said optical axis to accommodate said display unit and said autorefractor unit.

The control unit may be configured and operable to simultaneously operate said eye inspection units associated with both the user's eyes to determine said data inductive of at least one of eye accommodation to object in close proximity, convergence of line of sight of the user's eyes and a level of fusion of image data received by both eyes of the user.

Said control unit may comprise an image display module connectable to display units of right and left eye inspection units and configured to generate image data for display by said right and left display unit to provide desired three-dimensional image display to the user, said image data comprises at least one target object.

The control unit may also comprise an image distance controller connectable to the right and left display units to thereby operate the corresponding optical path units to adjust light ray propagation and thereby direct light rays to provide image display from a desired distance to the user.

The image distance controller and the optical path units may be configured and operable to provide image display associated with infinite distance to a distance of a few centimeters from the user's eyes.

The image distance controller may be configured and operable to generate image data corresponding to an object located at certain distance from the user's eyes, said certain distance being 1 meter or greater, and to update said image data to thereby gradually bring said object closer to the user's eyes, to thereby enable inspection of eyes' accommodation and convergence with respect to objects at close distance.

The control unit may comprise an eye orientation analyzer connectable to eye tracking units of said right and left eye inspection modules, said eye orientation analyzer is configured and operable for receiving data about orientation of right and left eyes of the user and data about location and distance of displayed image from said image distance controller, and for processing said data to determine correlation between actual orientation of the user's eyes and location of a target object in the displayed image with respect to the user's eyes.

Additionally or alternatively, said control unit may comprise an eye accommodation detector, the eye accommodation detector is connectable to the autorefractor units of said right and left eye inspection units and configured and operable for receiving therefrom data about optical power of right and left eyes of the user and data about location and distance of displayed image from said image distance controller, and for processing said data to determine correlation between optical power of the user's eyes with respect to distance of a target object in the displayed image.

Further, said control unit may comprise an eye condition analyzer module configured and operable for receiving data about correlation between determined eye state and anticipated eye state to thereby determine abnormality level of said correlation.

The control unit may also comprise an eye condition analyzer module configured and operable for receiving data about correlation between determined and anticipated eye orientation from said eye orientation analyzer and correlation between determined and anticipated optical power of the user's eyes from said eye accommodation detector and to determine data about eye condition, said data comprises at least one of the following: minimal object distance associated with eye accommodation, minimal distance associated with eye convergence, state of image fusion of user's at minimal distance of focus.

According to some embodiments, the eye inspection units may further comprise corresponding macular camera units located along general optical axis of the corresponding eye, said macular camera units being configured and operable to collect light arriving from the corresponding eye to thereby generate image data corresponding to a region around macula of the corresponding eye.

The control unit may also further comprise an image analyzer module, said image analyzer module being connectable to said macular camera unit for receiving image data of said region around the macula of the user's eyes and for processing said image data to determine at least one of existence, number, size and color of drusens in the user's eye.

According to one other broad aspect of the invention, there is provided a method for use in eye inspection of a user, the method comprising: presenting to a user image data corresponding to one or more specific objects; varying said image data to bring the one or more objects from a first distance from the user to a second distance being closer to the user than the first distance gradually; determining orientation of the user's eyes while following said one or more object moving from said first distance to said second distance; determining optical power of the user's eyes while following said one or more object moving from said first distance to said second distance; determining one or more distances of the object, corresponding to variation of orientation of one or more eye of the user with respect to object relative location or variation of optical power of one or more of the user's eyes exceeding corresponding predetermined threshold with respect to at least one of location and distance from the object.

Said presenting image data may comprise: generating image data to be presented, said image data comprises at least one distinct object and a relatively uniform background; and transmitting said image data to a display system configured to display said image data in a virtual three-dimensional display.

Said varying said image data may comprise changing position of the one or more objects in the image data to provide virtual three-dimensional display effect.

According to some embodiments, said varying said image data may comprise providing data about distance of the objects from the user to an optical system and varying configuration of said optical system to thereby affect light propagation from a display unit to the user's eye in accordance with a desired distance to an image plane of said optical system.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 7A shows image of drusen on the retina and FIG. 7B exemplifies detection of drusen according to some embodiments of the invention.

DETAILED DESCRIPTION OF EMBODIMENTS

Figure 1:
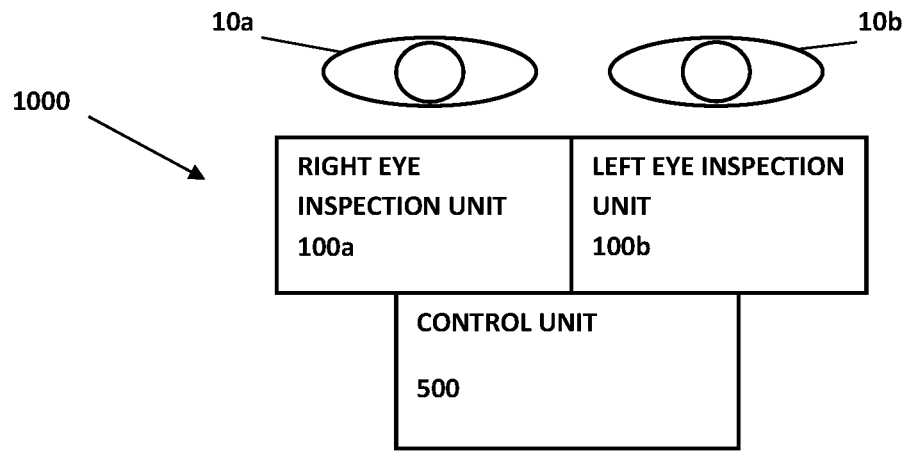
FIG. 1 schematically illustrates a system for use in eye inspection and diagnosis according to some embodiments of the invention.

Reference is made to FIG. 1, schematically illustrating a system 1000 for use of diagnosis of eye related conditions according to the present invention. The system 1000 generally includes a pair of eye inspection units 100a and 100b configured to inspect user's right and left eye 10a and 10b, and a control unit 500 configured for simultaneously operating the eye inspection units 100a and 100b and for processing and analyzing data about eye conditions received from the eye inspection unit s 100a and 100b. The system 1000 may generally be configured to be a head-mounted system, where the control unit 500 may be located within a common frame or external thereto while being connected to the head-mounted eye inspection units 100 through wired or wireless connection. Alternatively, the system may be configured to be stationary system, where the user/patient may sit in front of the eye inspection units 100.

The system 1000 is generally configured for inspection of user's eyes to provide data about at least one of accommodation of the eyes' optical power to objects at close distance, convergence of the eyes toward an such object at close distance, brain operation to fuse image data collected from the two eyes for near objects/scenes as well as to provide image data of internal regions of the eyes and especially of the macular region. More specifically, the control unit 500 is configured and operable to operate the corresponding eye inspection units 100 to provide image display to the user, and to collect data about eye movement and optical power of the eyes in response to the deployed image(s). The image display is provided by display units located in each of the eye inspection units 100 to thereby provide three-dimensional effect of the displayed image(s). Thus, the system of the present invention provides numerical objective data where the conventional diagnostic techniques relay on physician interpretation. Thus the technique of the invention may provide data that can be stored and compared with additional tests to follow changes in patient's condition without the need to relay on physician memory and/or personal interpretations of written results.

Figure 2:
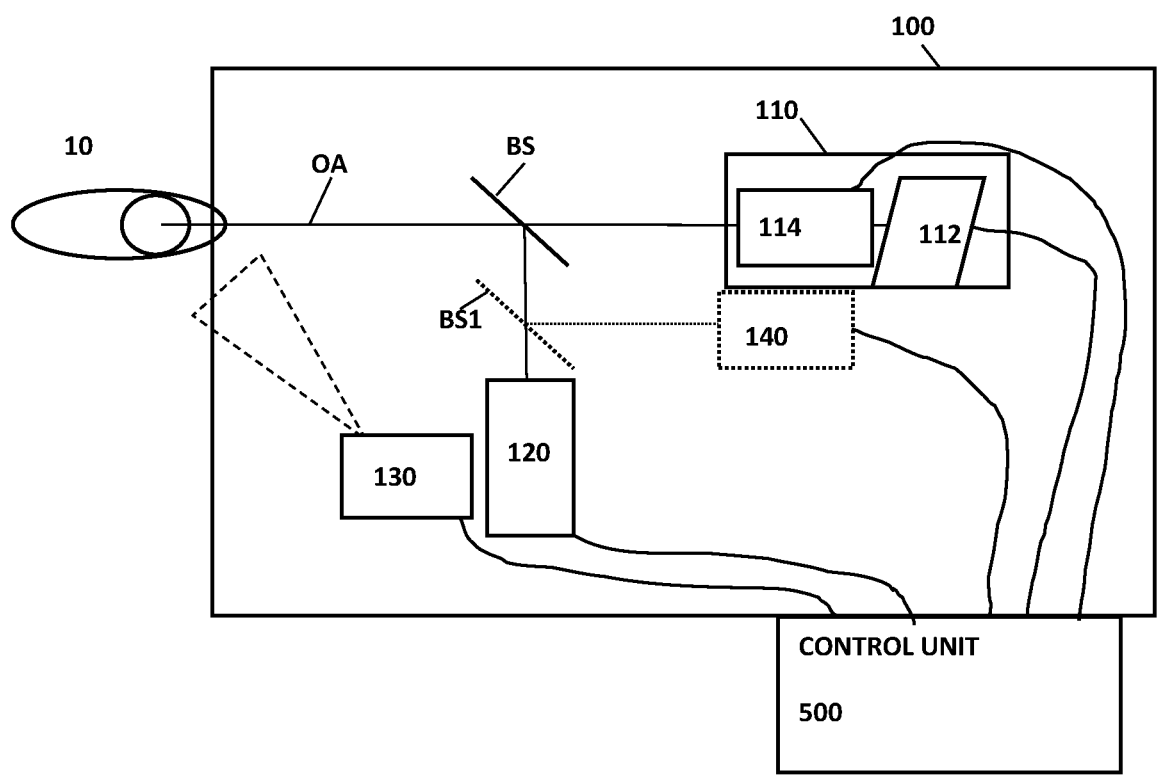
FIG. 2 schematically illustrates an eye inspection unit according to some embodiments of the invention.

Reference is made to FIG. 2 illustrating schematically a configuration of an eye inspection unit 100 according to some embodiments of the invention. The inspection unit is generally configured to be connected to and operated by a control unit 500 and includes a display unit 110, and optical power detection unit 120 (typically an autorefractor/autorefractometer unit) and an eye tracking unit 130. In some embodiments the eye inspection unit 100 may also include a macular imaging unit 140 configured to collect image data of internal regions of the users' eye, typically of the macular region. The display unit 110, optical power detection unit 120 and macular imaging unit 140 (when used) are generally configured to be located along optical axis OA of the eye 10. More specifically, the eye inspection unit 100 may include a beam splitter BS configured to enable location of the display unit 110 and the optical power detector 120 along optical axis OA of the eye 10. Additionally in some embodiments, an additional beam splitter BS1, which may also include a raster unit, may be located along the optical path between beam splitter BS and the optical power detector 120. This is to allow locating the macular imaging unit 140 along optical axis OA of the eye 10. Further, the second beam splitter BS1 may be configured also as a raster unit connectable to the control unit 500 to thereby enable following of the eye's 10 orientation to enable the optical power detector unit 120 and the macular imaging unit 140 to follow optical axis OA of the eye 10 when the eye is moving to provide reliable optical power detection and allow imaging of the macular region.

The display unit 110 is configured to receive data about images to be displayed so as to appear to the user as located is selected distances by virtual three-dimensional display from the control unit 500 and to provide corresponding display to the user. To this end the system 1000 utilizes two eye inspection unit 100 simultaneously providing separate display to each of the user's eyes. In some embodiments the display unit 110 may include a display panel 112, e.g. a screen, configured to provide display of desired images and an optical path unit 114 configured to vary location of a virtual image plane, thereby affecting light propagation from the display panel 112 towards the user's eye 10 to appear as if arriving from a desired distance. This allows the system 1000 to utilize display units 110 of both eye inspection units 100 to provide "real" three-dimensional display experience in the meaning that light propagation from displayed objects actually mimics the corresponding distances and requires the user's eyes to adjust optical power of the eye's lens to the distance.

The optical power detector 120 is configured to provide measured data indicative of optical power of the eye's 10 lens. The optical power detector 120 may typically be an autorefractor (autorefractometer) unit configured for shining a pattern in infra-red illumination into the user's eye and detect reflected light from the retina. The autorefractor/autorefractometer unit 120 is further configured for collecting returned light from the user's eye and for processing data about the collected light to determine data about optical power of the lens of the eye (cornea). In this connection it should be noted that the configuration and operation technique of autorefractor/autorefractometer units is well known in the art and is briefly described herein for completeness. Generally, an autorefractor/autorefractometer unit is configured to shine a pattern (or a few spots) of light in a predetermined wavelength such as IR, into the user's eye and vary optical power of a collection path thereof to provide high contrast of collection of light reflected from the retina. Typically an autorefractor/autorefractometer unit may scan optical power for collection assuming that the optical power of the user's eye is between +20 and −20 diopter thereby covering almost the entire possible range in a human eye. However, as known in the art, a typical autorefractor unit is configured for determining optical power of the eye's lens when focusing at objects located at large distance from the eye, generally resembling infinite distance and typically more than a few meters. In the system 100 according to the present invention, however, the autorefractor unit 120 is generally configured to determine optical power of the eye while focusing at objects located at close distances, typically 1 meter or less.

Generally, the optical power detector 120 is located to be aligned with optical axis of the user's eye at certain predetermined orientation thereof. In some embodiments, the optical power detector 120 may be configured to follow gaze direction of the user, based on corresponding data received from the eye tracking unit 130. Either having fixed direction or configured to follow gaze direction, the optical power detector 120 is configured to receive data about eye orientation from the control unit 500, or directly from the eye tracking unit 130, indicative of eye orientation. When configured with fixed direction, the optical power detector 120 received data about gaze direction to operate when the corresponding eye is in the correct orientation for detection of optical power thereof. Additionally, according to some embodiments, the control unit 500 may be configured and operable to generate suitable image display 112 to thereby direct the user's eyes to the desired orientation for operation of the optical power detector 120.

As indicated, the eye tracking unit 130 is configured and operable for generating data indicative of orientation and/or location of the user's eyes, and for providing this data to the control unit 500. The eye tracking unit may include a camera unit and may include, or be connectable to a local processor unit being a part of the eye tracking unit 130 or of the control unit 500. The camera unit is typically directed to collect image data about the corresponding eye. Data indicative of the image data is transmitted to the local control unit for image processing and detection of location of the pupil with respect to the eye to determine data about location and orientation of the pupil, thereby determining gaze direction of the user's eye.

Further, as indicated above, the eye inspection unit 100 may also include a macular camera unit 140. The macular camera unit is generally a camera unit including a lens arrangement and a detector array (not specifically shown) and configured for collecting image data indicative of a region of the user's retina, and more specifically a predetermined relative region around that macula of the user. To this end the macular camera unit 140 may also include a light source unit (e.g. infra-red light source, or visible light source, e.g. red light) configured to illuminate the macular region of the user's eye, typically a region with radius of 1-10 mm, or 2-6 mm or 3-5 mm, around the macula of the user's eye. The camera unit is configured with optical lens arrangement is configured to collect light returning from the macula and generate a corresponding image on the detector array to thereby generate image data about the macula of the user.

The macular camera unit 140 may typically be a simple camera configured to detect light of red and/or IR wavelengths and include a corresponding light source for illuminating the retina. The optical arrangement of the camera 140 may be aligned with certain optical axis OA of the eye inspection unit 100 to provide relatively narrow field of view associated with a region of the macula of the user's eye 10.

Similarly to the optical power detector 120, the macular camera unit 140 may be configured to follow gaze direction of the user, or be configured at a fixed direction and operable when the user's eye is oriented with a suitable gaze direction. In this connection, the optical power detector 120 and the macular camera unit may be located on a similar optical axis (OA) and configured with a second beam splitting unit BS1 configured to split light between the optical power detector 120 and the macular camera unit 140. Beam splitting unit BS1 may be configured as a 50:50 beam splitter or as a wavelength selective reflector/transmitter as the case may be.

Generally the system 1000, as illustrated in FIG. 1, including right and left eye inspection units 100a and 100b may be configured as a head mounted system, being integral with the control unit 500 or connected thereto via wired or wireless connection. In some embodiments, the system 1000 may be configured to be mounted or positioned on a table or any other stand configured and located such that the user may comfortably locate his head in the appropriate location for eye inspection.

The control unit 500 is connectable to both right and left eye inspection units 100a and 100b and configured to simultaneously operate the eye inspection units 100a and 100*b* to provide suitable display to the user and determine data about one or more eye conditions in accordance with one or more eye parameters corresponding to the displayed data. Such one or more eye parameters may include one or more of orientation of the user's eye gazing at objects at near distance therefrom, accommodation of optical power of the eye for objects at near distances, a measure of fusion of images collected by the user's eyes for objects at near distance and a measure of macular condition associated with existence, number of and sizes of drusens on the macular region of the user's eyes.

Figure 3:
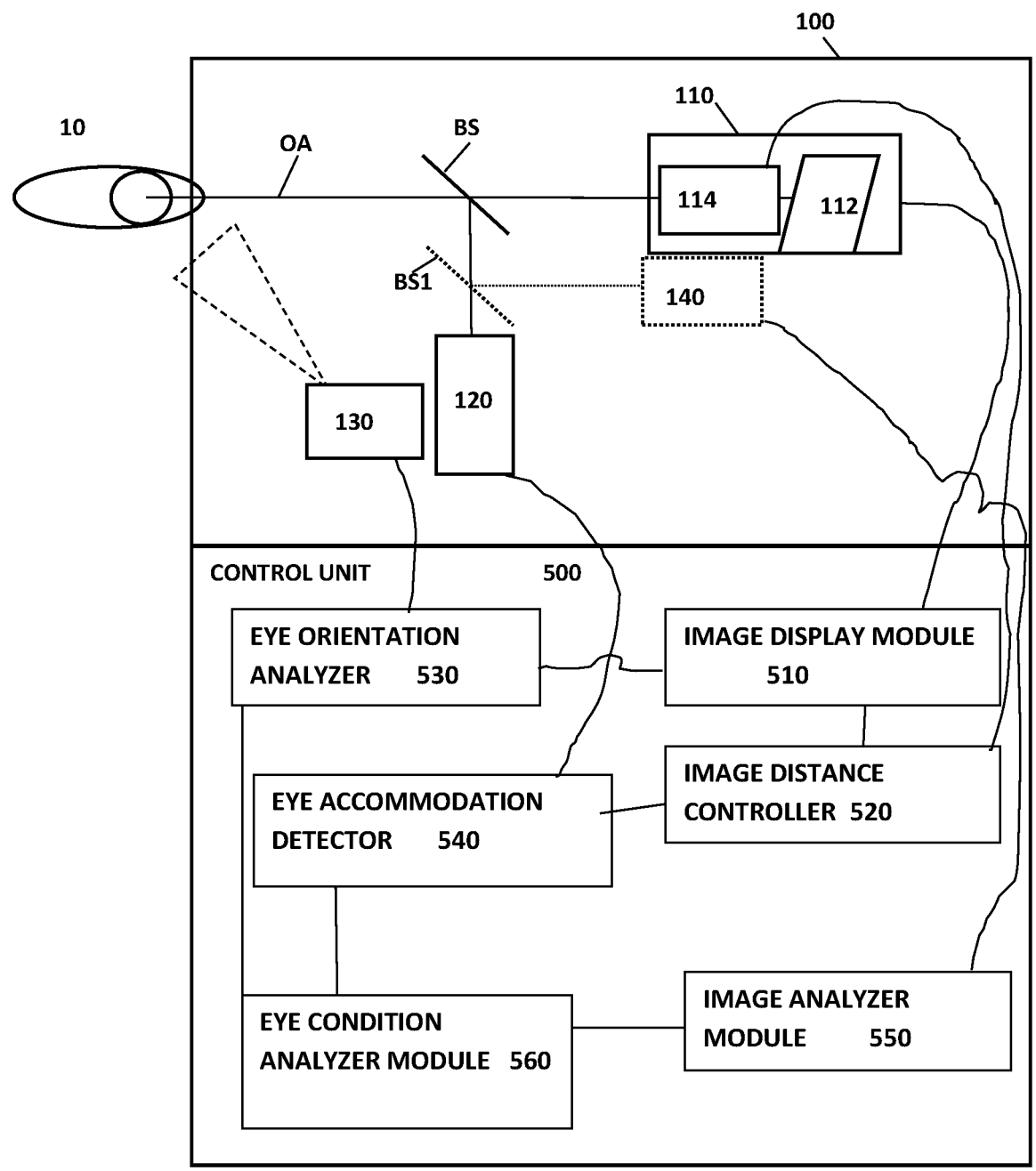
FIG. 3 illustrates schematically a configuration of a control unit and eye inspection unit according to some embodiments of the invention.

Reference is made to FIG. 3 illustrating a schematic configuration of the control unit 500 with respect to one of the eye inspection units 100. As shown the control unit 500 includes an image display module 510, image distance controller 520, eye orientation analyzer 530, eye accommodation detector 540, image analyzer module 550 and eye condition analyzer 560. In this connection it should be noted that the control unit may typically be configured as a processing unit and the above described modules may be hardware and/or software modules thereof. Further the control unit may generally include, or be connectable to one or more storage utilities (being local and/or remote), memory utility and input/output connection ports for network communication and user interface communication that are not specifically shown. The control unit is generally configured and operable to utilize and operate the right and left eye inspection units 100*a* and 100*b* to perform one or more tests and determine one or more parameters about conditions of user's eyes. More specifically, the control unit 500 is typically configured and operable to determine one or more parameters about one or more of eyes' orientation and optical power adjustment for objects in close distance, fusion of images collected by the right and left eyes at close distance and deposition of material at a region of the retina around the macular region of the eyes.

To this end, the control unit 500 typically operates the right and left eye inspection units 100*a* and 100*b* to display and image to both the right and left eyes of the user. The displayed images may typically contain certain background and one or more objects, where the background may preferably be relatively uniform and preferably do not contain distracting patterns that may attract the user's attention from the one or more objects. The display units of the right and left eye inspection units 100*a* and 100*b* are operated together to provide a three-dimensional effect showing the object as being located at a first distance, e.g. about 1 meter from the user, and moving towards the user. During virtual movement of the displayed object towards the user, the right and left eye inspection units may follow eye orientation of the user and/or optical power applied by the lenses of the user's eyes. Based on data indicative of the user's eye orientation and/or optical power for observing objects at different distances, the control unit may generate data about eye condition of the user for diagnostics by a physician or further processing.

Additionally, or alternatively, according to some embodiments of the invention, the control unit 500 may be configured and operable to operate the right and left eye inspection units 100*a* and 100*b* to provide certain display data to thereby direct the user's gaze to a desired location (optical axis), and to operate the eye inspection units to collect image data of at least a region of the user's retina.

Generally, as indicated above, the control unit 500 may include one or more modules, being software and/or hardware modules. To this end it should be noted that the description of the operation modules as described herein is exemplary and may differ based on structure of the processing utility of the control unit 500.

Figure 4A:
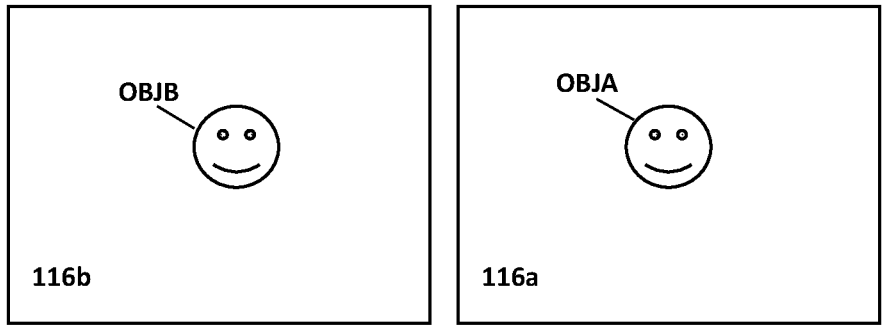
FIGS. 4A to 4C exemplify three-dimensional effect in image display the can be used in image display according to some embodiments of the invention.
Figure 4B:
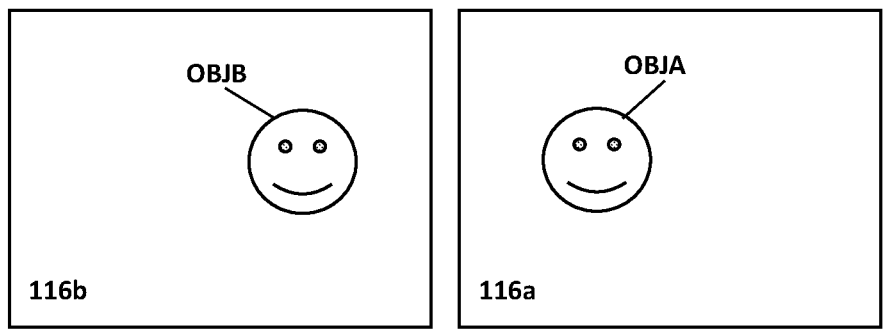
Figure 4C:
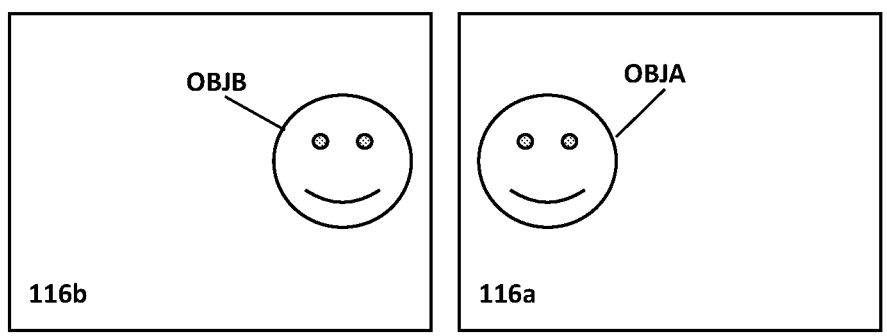

The image display module 510 is configured and operable to generate image data and transmit the generated image data to the display units 110 of the right and left eye inspection units 100. As indicated above, the image data typically includes a relatively uniform background and one or a few objects selected to attract the user's attention. The objects may typically correspond to face of random or selected person, smiley, tree, car, butterfly, or any other animal, geometric shape etc. The image display module 510 is typically configured to generate right- and left-eye image data to be displayed by the corresponding right and left display units 110 to provide virtual three-dimensional (3D) effect to the user. This is exemplified in FIGS. 4A to 4C illustrating image displays 116*a* and 116*b* of the right and left display units side by side as would be viewed by the user. Within the frame of each of the displayed images, relative location of the objects OBJA and OBJB varies to provide virtual 3D effect. It should be noted that in typical 3D displays, relative locations between objects at different virtual distance vary. However, according to the technique of the invention, a single or only a few images are displayed to the user. Further, the technique of the present invention is typically directed at providing objects that are virtually at close proximity to the user, in many configurations in distances of 6 meter and below, or 1 meter and below, and is some configuration providing displayed object at virtual distance of 30 cm from the user, or of 20 cm or 10 cm from the user. At these distances and utilizing relatively uniform background, the displays units are configured to show the object at locations that correspond to convergence of the user's eye towards the object. This is shown in FIGS. 4A to 4C; in FIG. 4A the object is shown at a relatively large distance, e.g. 1 meter or more; in FIG. 4B the object is shown at a closer distance, e.g. 50-60 cm; and in FIG. 4C the object is shown as closer distance, e.g. 15-30 cm from the user. As shown, the closer the object is, the bigger the display area taken by the object. Additionally the object representations for the right and left eyes OBJA and OBJB are closer to the central region between the eyes, thereby requiring the user to converge eye orientations to view the object.

Additionally to the object orientation effect providing virtual 3D display, the technique of the invention also provide for virtual optical distance effect. To this end the display unit 110 of each of the eye inspection units 100*a* and 100*b* may generally be configured to include a display panel 112 providing the image display and an optical path unit 114 configured to affect light propagation from the display panel 112 and towards the user's eyes 10 to thereby determine virtual distance between the displayed images and the user's eyes 10. Further, the control unit 500 may include an image distance controller 520. The image distance controller 520 is configured and operable to receive input data about image to be displayed to the user and generate data indicative of a distance between the presented object and the user's eye. The image distance controller 520 is configured to operate the optical path unit 114 to vary light propagation from the display panel 112 to the user's eye 10 to provide virtual axial displacement of the visible image in accordance with desired object distance. Such object distance may typically be between 1 meter from the user and as close as about 10 cm from the user.

Figure 5A:
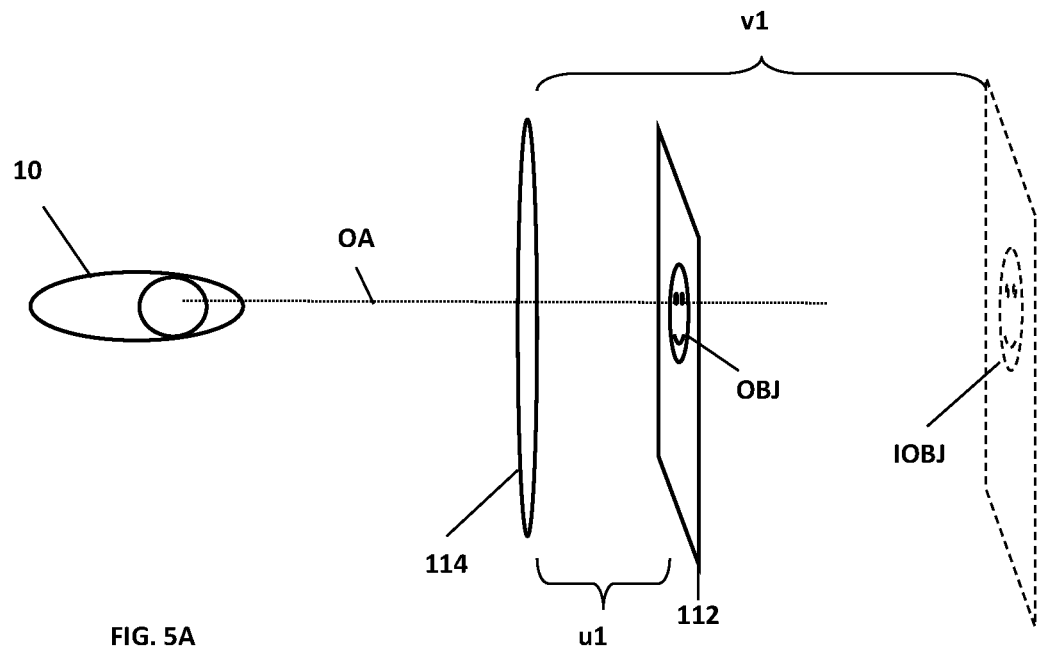
FIGS. 5A and 5B exemplify optical path system configured to vary effective distance of display according to some embodiments of the invention.
Figure 5B:
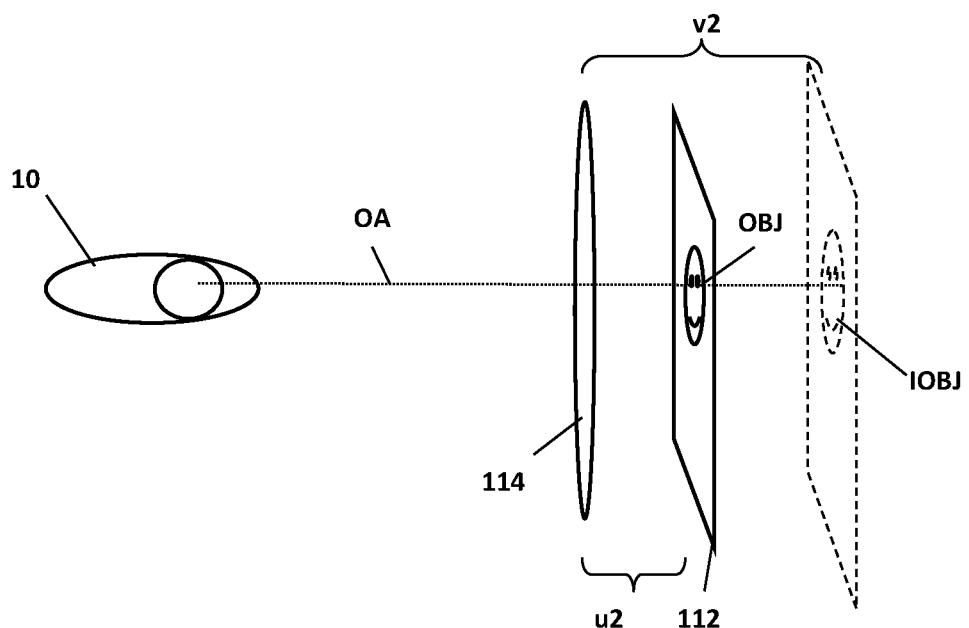

Exemplary operation of the optical path unit 112 is illustrated in FIGS. 5A and 5B showing an optical lens unit 114 located in optical path of light from a display panel 112 and the user's eye 10 where the optical unit 114 is configured to make object displayed on the panel 112 to appear at selected distanced from the eye 10. It should be noted that the technique illustrated in FIGS. 5A and 5B is general and the optical path unit 114 may include additional lens elements in accordance with optical design of the unit.

Specifically, FIG. 5A and FIG. 5B illustrate an image of an object OBJ shown on the display panel 112 located at a fixed position with respect to the user's eye 10. The optical unit 114, exemplified in this figures as a lens having positive focal length (e.g. magnifying lens), is located in optical path between the display panel 112 and the eye 10, and is configured to be moveable along the optical axis OA to vary distance between the display panel 112 and the lens 114. In FIG. 5A the lens is shown as being at distance u1, being smaller than focal length of the lens, from the display panel thereby forming a virtual image plane at distance v1 from the lens. In FIG. 5B the lens 114 is moved to distance u2 from the panel, smaller than u1, and forming the virtual image plane at distance v2 from the lens. The variation in lens location and location of the virtual image plane actually varies virtual distance between the objects as seen by the user IOBJ. When the distance between the lens 114 and the display panel 112 is equal to the focal length of the lens 114, the object appears at infinite distance, when the distance between the lens 114 and the display panel 112 is reduced, the object appears to come closer. Generally the location of the virtual image plane is defined by the lens equation $1/f=1/u+1/v'$, where f is the foal length of the lens 114 (or effective focal length of a lens arrangement), u is the distance between the lens and the object, and v is the distance between the lens and the image. As u<f in this case, v is generally negative, providing virtual image plane. This configuration of the display unit 110 requires that the optical power of the user's eyes will adapt to distance of the object thus enabling measurement of optical power variations in the eye 10.

Figure 6A:
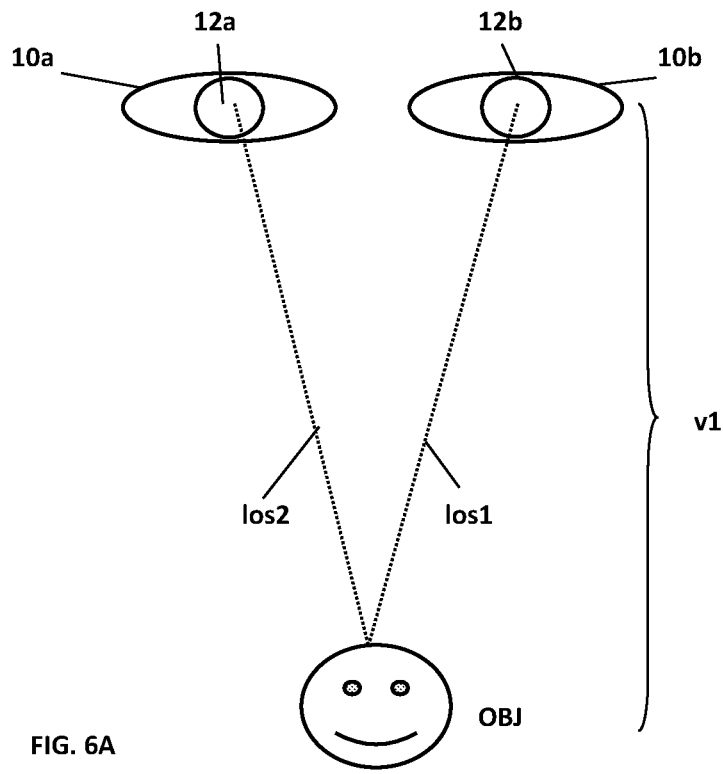
FIGS. 6A to 6C exemplify eye orientation with respect to objects at close distance (FIGS. 6A and 6B) and breakage of eye orientation and fusion of image data at certain distance (FIG. 6C)
Figure 6B:
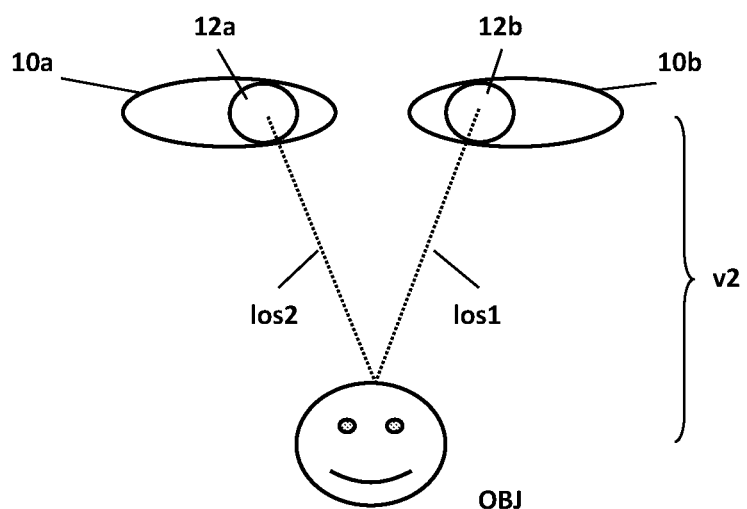
Figure 6C:
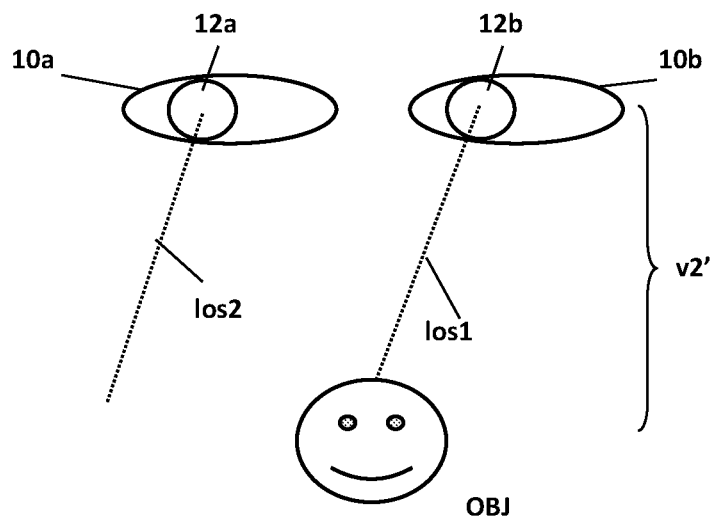

Returning to FIG. 3, the control unit 500 may also include an eye orientation module 530. The eye orientation module 530 is connected to the eye tracking unit 130 and configured to receive data about location of the user's pupils to determine gaze direction of the user's right and left eyes. The eye orientation module may generally also be configured to receive data about displayed image from the image display module 510 to determine a relative direction between the gaze direction of the eyes and location of an object presented on the display 110. In some configurations, the eye orientation module may generate data indicative of a measure of displacement between gaze direction of the user's eye and virtual location of the displayed object thereby determining if the eye is indeed focusing on the object or is shifted to a different direction. Variation of gaze directions of the user's eye is exemplified in FIGS. 6A to 6C schematically illustrating virtual location of a displayed object OBJ with respect to gaze directions los1 and los2 of the user's right and left eyes 10a and 10b. The gaze direction is exemplified in the figures based on location of the pupils 12a and 12b.

The control unit 500 may also include an eye accommodation detector 540 configured and operable for receiving data about object distance from the image distance controller 520 and data about optical power of the user's eye from the optical power detection unit 120. The eye accommodation detector 540 is configured to determine a relation between distance from the user's eyes to the object and the optical power provided by the eye to thereby indicate whether the eye is optically focusing on the object or the object is seen blurry.

The eye condition analyzer module 560 is configured and operable to receive data about measured eye orientation with respect to object location from the eye orientation analyzer 530 and data about eye accommodation with respect to object distance from the eye accommodation detector 540, and to process and analyze this data to determine one or more parameters associated with eye condition. In particular, the eye condition analyzer module 560 may determine one or more eye parameters generally associated with computer vision syndrome (CVS), but it should be noted that such eye parameters may also be used to determine and diagnose various other eye conditions.

In this connection, the eye condition analyzer module 560 may be configured and operable to operate the right and left eye inspection units 100, by operating the different modules of the control unit 500, to perform a diagnosis test on user's eye condition. Generally, after receiving indication that a user is in place and ready to start a test, the eye condition analyzer module 560 may operate the image display module 510 and distance controller 520 to generate image data and present the image data to the user as being in a distance of 1 or more meters from the user, i.e. relatively large distance. The image data may generally include a relatively low contrast background and a main object selected to draw the user's attention thereto. The eye orientation analyzer 530 and eye accommodation detector 540 are operating continuously to determine relation between orientation of the user's eye with respect to location of the main object being displayed and optical power of the user's eye with respect to distance to the object.

During the test, the eye condition analyzer module 560 operates the image display module 510 and distance controller 520 to vary the displayed data and distance such that the main object is becoming closer and closer to the user's eyes. To this end the object's location on the screen varies as shown in FIGS. 4A to 4C as well as the propagation path of light from the display panel 112 to the user's eye 10 as exemplified in FIGS. 5A and 5B. Generally at certain minimal distance between the object and the user's eye, the user's eye can no longer efficiently focus on the object. This may be a result from one or more conditions as follows. At certain distance between the object and the eye (e.g. below 40 cm or below 20 cm depending on user's condition) the eye can no longer vary its orientation inwards to maintain visible line with the object. At certain other (or similar) distance, the eye can no longer adapt its lens' optical power to properly focus on the object, when it is too close. At certain distance, the user's brain may give up on one of the eyes and stops processing data provided by this eye. At this point the eye that is no longer used will return to rest position and stop following the object.

These three parameters, relating to eye convergence (orientation), accommodation (optical power) and fusion (of images by the brain) provide important parameters that may assist a physician in diagnosis of various eye related issues such as CVS. The present technique provides a simple and effective technique for diagnosis of such eye conditions and may thus be used to assist in patients' diagnosis and treatment and indicate eye related issues even when the symptoms are not necessarily eye related (e.g. headaches).

As indicated above, in some configurations, the control unit may also include and image analyzer module 550 configured and operable to receive image data from the macular camera unit 140 and to process and analyze the received image data to determine at data about corneal drusen deposition. In this connection reference is made to FIGS. 7A and 7B showing image data of the macular region of a retina of a patient (FIG. 7A) and exemplifying image processing and analysis performed by the image analyzer module 550 (FIG. 7B).

Figure 7A:
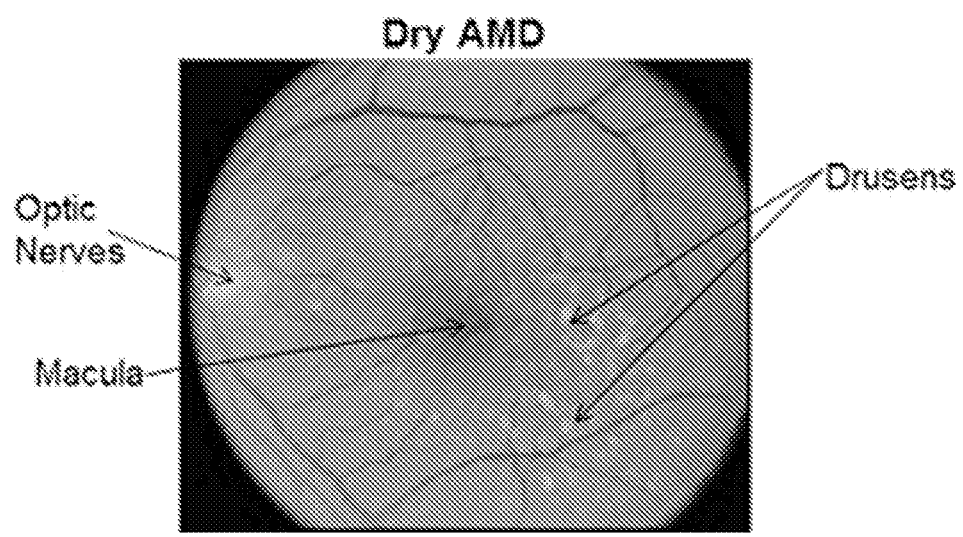
FIGS. 7A and 7B exemplify detection of drusen in retina of the user.
Figure 7B:
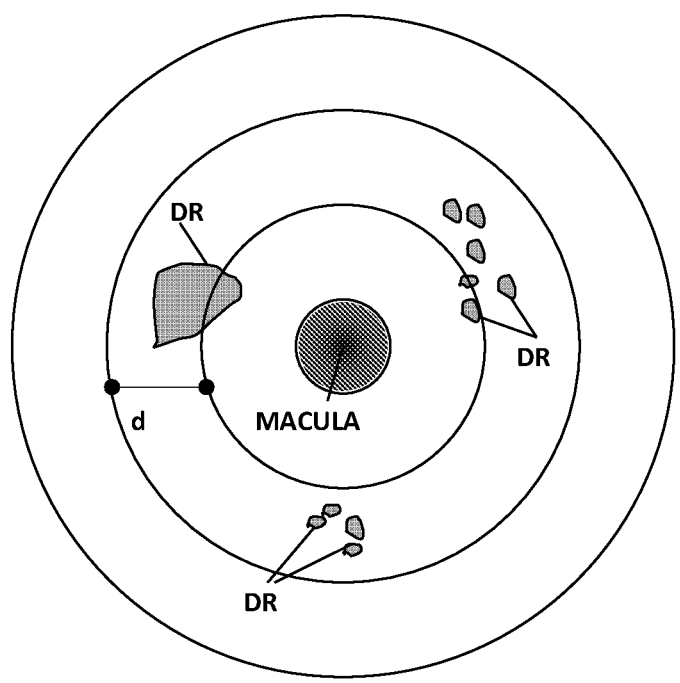

FIG. 7A shows an image of macular region of the retina of a patient having Age-related Macular Degeneration (AMD) in dry stage. The image shows that macula of the eye at the center, the optic nerve transmitting data to the brain and a plurality of drusens around the macula. According to the American Academy of Ophthalmology drusen are yellow deposits located under the retina, which is the light-sensitive tissue at the back of the eye and are made up of lipids, a fatty protein. While drusen likely do not cause AMD, their presence increases a person's risk of developing AMD. There are different kinds of drusen. "Hard" drusen are small, distinct and far away from one another. This type of drusen may not cause vision problems for a long time, if at all. "Soft" drusen are large and cluster closer together. Their edges are not as clearly defined as hard drusen. This soft type of drusen increases the risk for AMD.

The image analyzer module 550 is configured and operable for receiving image data of the macular region from the macular camera unit 140 and for processing and analyzing the image data to determine existence of drusen around the macular region of the user's eye. The image analyzer module 550 utilizes image processing techniques for identifying regions of the retina having reflectance properties different than those of the rest of the retina to determine existence of drusen on the retina. Further, the image analyzer module 550 may also determine at least one of the following: number, location, sizes and color of drusen on the retina. This is exemplified in FIG. 7B showing a number of small drusen DR and a single larger drusen detected around the macula. Generally the image analyzer module (550 in FIG. 3) may generate data about number, size, location (e.g. with a radius or distance d from the macula, at certain angular region) and/or color of drusen in the form of image data as well as in the form of numerical data. The data about drusen in patient's retina may be used for diagnosis by a physician as well as stored for later use as reference to follow patient disease progress and/or response to treatment. It should be noted that such data about drusen existence on the retina may be used for various other diagnosis and for obtaining research data about one or more of the following: Alzheimer's disease, Atherosclerosis as well as other conditions. Further the technique of the invention provides a simple a reliable detection and diagnosis technique providing measurable data that does not depend on physician's interpretation and that may be stored for further analysis and periodic follow up.

Thus, the present invention provides a system for use in diagnosis of one or more eye related issues. As indicated above, the system may be configured as a head-mounted system or a desk-mounted system, and provide simple and non-invasive measurement of various eye parameters. The technique of the invention utilizes display technique used for obtaining patients' attention to simplify diagnosis process and provide reliable and objective data that may be stored for follow-ups and comparisons. Those skilled in the art will readily appreciate that various modifications and changes can be applied to the embodiments of the invention as hereinbefore described without departing from its scope defined in and by the appended claims.

The invention claimed is:
1. A system for use in diagnostics of eye condition of a user comprising:

a pair of eye inspection units configured for inspection of each of the user's eyes; said pair of eye inspection units including:
(a) a display unit comprising a display panel configured to display one or more selected images to right and left eyes of the user, and
(b) an optical path unit located in optical path between the display panel and said right and left eyes and configured for selectively controlling light ray propagation towards said right and left eyes,
(c) an eye tracking module configured to generate data about of location and orientation of said right and left user's eyes thereby providing data indicative of a gaze direction of each of said right and left eyes and
(d) an optical power detection unit configured and operable for obtaining and determining data indicative of an optical power of said right and left eyes; and a control unit configured and operable to operate said pair of eye inspection units to thereby determine data indicative of at least one of eye accommodation to an object in close proximity, convergence of line of sight of the user's eyes and a level of fusion of image data received by both eyes of the user said control unit including:
(a) an image distance controller operationally connected to said optical path unit to adjust light ray propagation and thereby direct light rays to said display to provide a virtual desired distance of said one or more selected images to said right and left eyes,
(b) an eye orientation analyzer operationally connected to said eye tracking module for receiving said gaze direction and operationally connected to said image distance controller for receiving said virtual distance from said image distance controller, and configured for determining a orientation correlation between said gaze direction and a location of said one or more selected images with respect to said right and left eyes,
(c) an eye accommodation detector operationally connected to said optical power detection unit for receiving said optical power of said right and left eyes and to said image distance controller for receiving said virtual distance and configured for processing said eye data to determine a power correlation between said optical power of said right and left eyes with respect to said virtual distance of said one or more selected images from said right and left eyes and
(d) an eye condition analyzer module configured and operable for:
receiving said power correlation and
receiving said orientation correlation
and estimating an eye condition from comparing said orientation correlation to an anticipated eye orientation and said power correlation to an anticipated optical power including computing at least one of the following: a minimal object distance associated with eye accommodation, a minimal distance associated with eye convergence, and a state of image fusion of the user at a minimal distance of focus.

2. The system of claim 1, wherein optical power detection unit includes an autorefractor and wherein said display unit and said optical power detection unit are located along a general optical axis of at least one said right and left eyes, said pair of eye inspection units further including a beam splitting module configured for splitting said optical axis to accommodate said display unit and said optical power detection unit.

3. The system of claim 1, wherein said control unit is configured and operable to simultaneously operate said pair of eye inspection units to determine said power correlation for an object in close proximity, said orientation correlation and a level of fusion of image data received by both of said right and left eyes.

4. The system of claim 1, wherein said display unit includes a right eye display unit and a left eye display unit and said control unit comprises a image display module connectable to said right eye display unit and said left eye display units; said image display module configured to generate image data for display by said each of said right eye display unit and said left eye display unit to provide desired three-dimensional image display to the user, said image data comprising at least one target object of said one or more selected images.

5. The system of claim 1, wherein display unit includes a left eye display and a right eye display and said image distance controller is connected to the right eye display and left eye display to separately control said one or more selected images displayed therein to adjust light ray propagation and thereby direct light rays to provide image display from a desired said virtual distance to the user.

6. The system of claim 1, wherein said image distance controller and said optical path unit is configured and operable to provide said virtual distance ranging between infinite distance to a distance of a few centimeters from said right and left eyes.

7. The system of claim 6, wherein said image distance controller is configured and operable to vary said virtual distance from 1 meter and to gradually reduce said virtual distance, to thereby enable inspection of eyes' accommodation and convergence with respect to objects at close distance.

8. The system of claim 1, wherein said eye condition analyzer module is configured and operable for comparing said power correlation to an anticipated eye state to thereby determine abnormality level of said power correlation.

9. The system of claim 1, wherein the pair of eye inspection units further include
    (e) a macular camera configured and operable to collect light arriving from said right and left eyes to thereby generate image data corresponding to a region around a macula of each of said right and left eyes.

10. The system of claim 9, wherein said control unit further includes:
    (e) an image analyzer module, said image analyzer module being connectable to said macular camera for receiving image data of said region around the macula of each of said right and left eyes and for processing said image data to determine at least one of existence, number, size and color of drusens in each of said right and left eyes.

11. The system of claim 1, wherein said eye inspection units are configured in a head mounted package.

\* \* \* \* \*